US011389185B2

(12) United States Patent
Golden et al.

(10) Patent No.: US 11,389,185 B2
(45) Date of Patent: Jul. 19, 2022

(54) DEVICES, SYSTEMS AND METHODS FOR TISSUE RESECTION

(71) Applicant: Boston Scientific Scimed, Inc., Maple Grove, MN (US)

(72) Inventors: John B. Golden, Norton, MA (US); Caleb A. Valdes, Lowell, MA (US); Austin G. Johnson, Hudson, MA (US); Chris Jicka, Upper Saddle River, NJ (US); Serena Scott, Worcester, MA (US); Michael K. Ford, Waltham, MA (US); Kyle P. Moore, Milton, GA (US); Janice Courtois, Clinton, MA (US); Prashanth Somasundaram, Boston, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 93 days.

(21) Appl. No.: 16/419,918

(22) Filed: May 22, 2019

(65) Prior Publication Data
US 2019/0357933 A1 Nov. 28, 2019

Related U.S. Application Data

(60) Provisional application No. 62/675,679, filed on May 23, 2018.

(51) Int. Cl.
*A61B 17/32* (2006.01)
*A61B 17/3205* (2006.01)
(Continued)

(52) U.S. Cl.
CPC .. *A61B 17/320016* (2013.01); *A61B 17/3205* (2013.01); *A61B 17/128* (2013.01);
(Continued)

(58) Field of Classification Search
CPC ........ A61B 17/320016; A61B 17/3205; A61B 2017/00269; A61B 2017/320064;
(Continued)

(56) References Cited

U.S. PATENT DOCUMENTS 7,955,340 B2  6/2011  Michlitsch et al.
8,863,748 B2  10/2014  Kuroda et al.
(Continued)

FOREIGN PATENT DOCUMENTS

WO   2008054617 A1   5/2008

OTHER PUBLICATIONS

International Search Report and Written Opinion for International application No. PCT/US2019/033595, dated Aug. 20, 2019, 11 pages.

*Primary Examiner* — Kathleen S Holwerda
*Assistant Examiner* — Uyen N Vo
(74) *Attorney, Agent, or Firm* — Seager, Tufte & Wickhem, LLP

(57) ABSTRACT

Exemplary embodiments of the present disclosure relate to devices, systems, and methods for tissue resection in a body lumen of a patient, and may include an elongate body having a cavity at a distal end and a tissue retractor extendable distally from the distal end of the elongate body. The tissue retractor may include an expansion mechanism. The expansion mechanism may include a plurality of arms each having a first end coupled around a distal cap and expandable radially outward from the distal cap such that an anchoring mechanism on a second end of the arms is engageable with selected tissue for resection of the body lumen. The tissue resection device may further include a tissue resecting device.

19 Claims, 17 Drawing Sheets

(51) Int. Cl.
   *A61B 17/00* (2006.01)
   *A61B 17/128* (2006.01)

(52) U.S. Cl.
   CPC ............ *A61B 2017/00269* (2013.01); *A61B 2017/00623* (2013.01); *A61B 2017/320064* (2013.01)

(58) Field of Classification Search
   CPC .......... A61B 17/00234; A61B 17/0218; A61B 17/1227; A61B 17/083; A61B 17/10; A61B 2017/00296; A61B 2017/12018; A61B 2017/00575; A61B 2017/00659; A61B 2017/00668; A61B 2017/00818; A61B 17/32053; A61B 17/3478; A61B 17/1285; A61B 17/128
   See application file for complete search history.

(56) References Cited

U.S. PATENT DOCUMENTS

| | | |
|---|---|---|
| 2002/0082614 A1 | 6/2002 | Logan et al. |
| 2003/0023260 A1* | 1/2003 | Bonutti .............. A61B 17/0218 606/192 |
| 2012/0232459 A1 | 9/2012 | Dann et al. |
| 2012/0296354 A1* | 11/2012 | Hsu ...................... A61B 17/068 606/153 |
| 2014/0081305 A1* | 3/2014 | Breznock .......... A61B 17/32053 606/184 |
| 2014/0277045 A1 | 9/2014 | Fazio et al. |
| 2015/0018848 A1* | 1/2015 | Kappel .............. A61B 17/1285 606/140 |
| 2016/0166243 A1* | 6/2016 | Wilson ............... A61B 17/3209 606/170 |

* cited by examiner

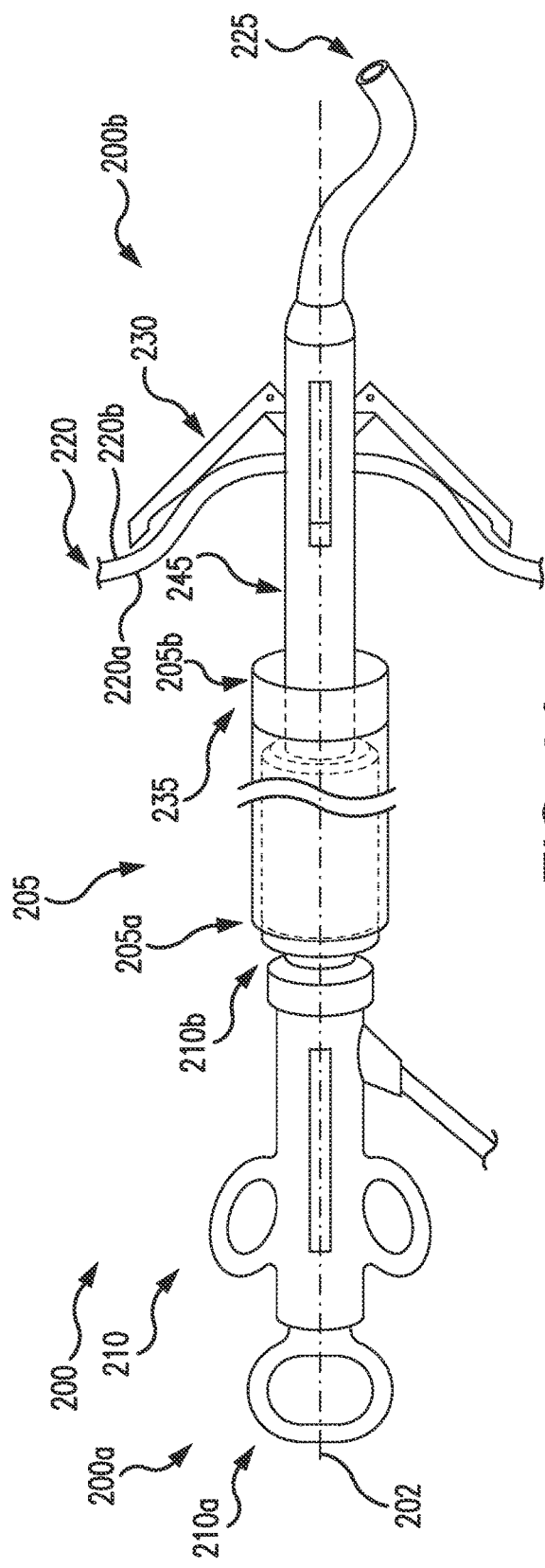
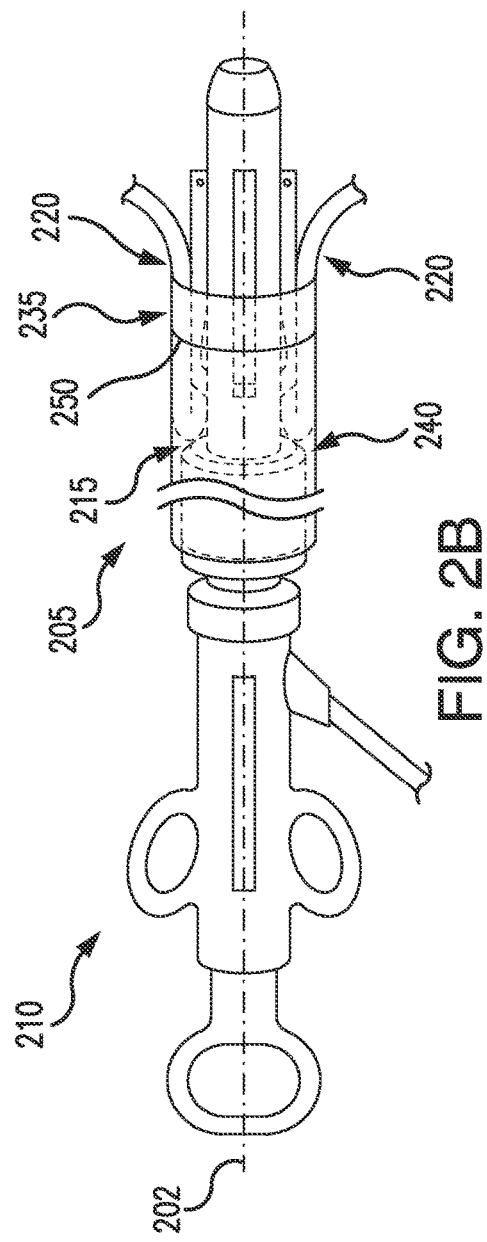
FIG. 2A
FIG. 2B

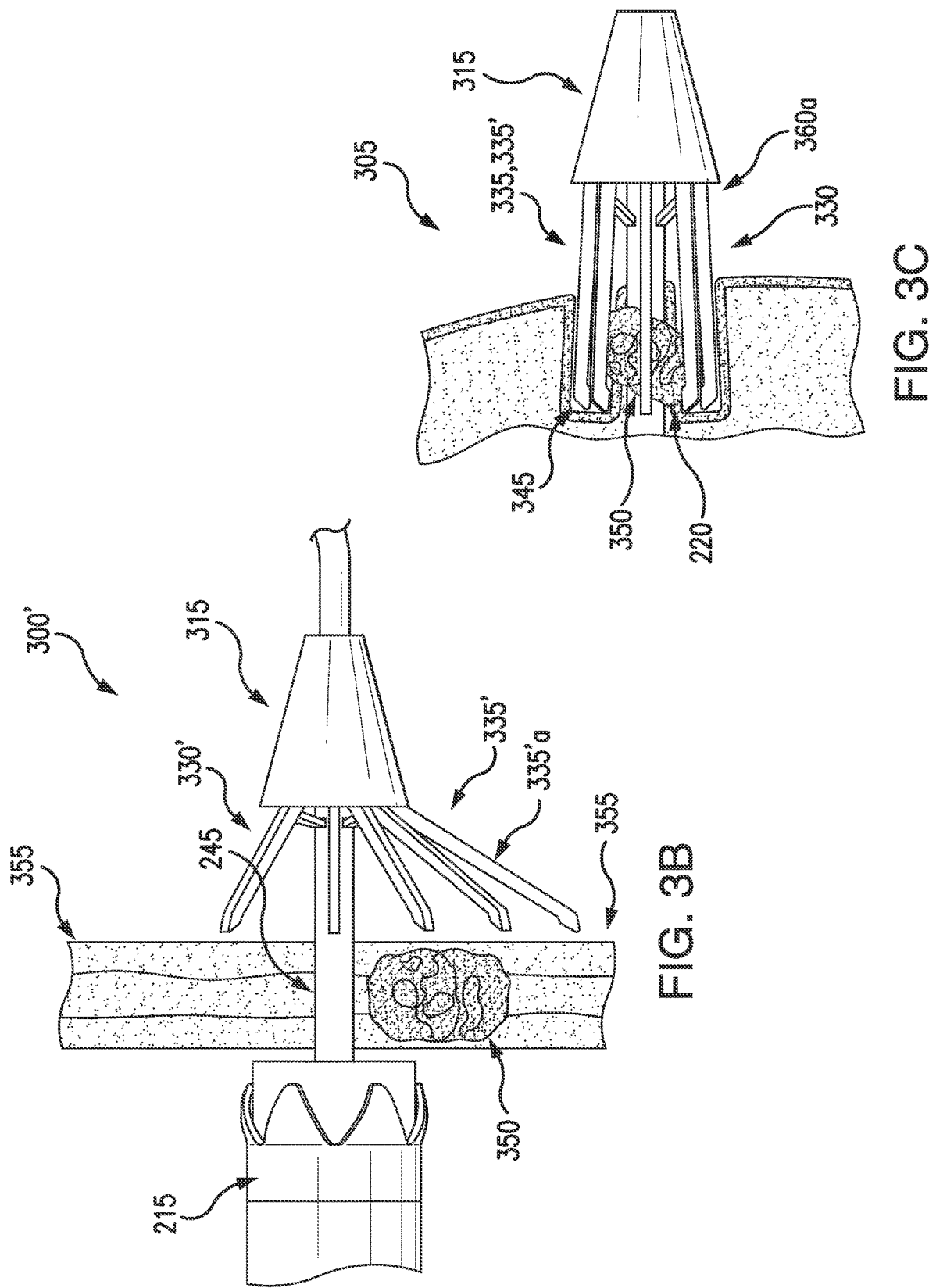

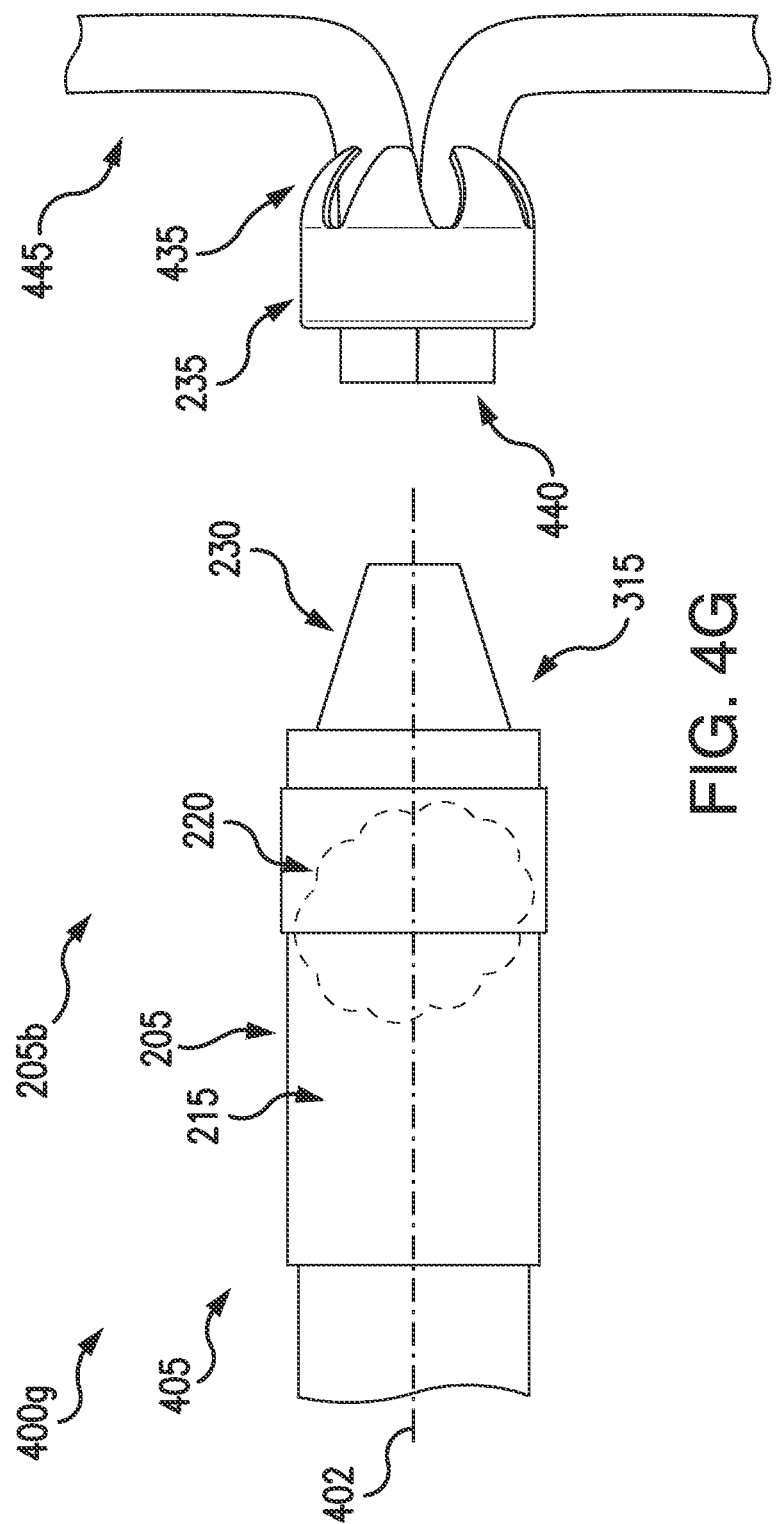

DEVICES, SYSTEMS AND METHODS FOR TISSUE RESECTION

CROSS REFERENCE TO RELATED APPLICATIONS

This application claims the benefit of priority under 35 U.S.C. § 119 to U.S. Provisional Patent Application Ser. No. 62/675,679, filed on May 23, 2018, which is incorporated by reference in its entirety for all purposes.

FIELD

The present disclosure relates generally to devices, systems, and methods for performing endoscopic procedures, and, more particularly, tissue resection devices for endoscopic mucosal resection (EMR) and/or endoscopic submucosal dissection (ESD) procedures, including such devices, system and methods to achieve partially or fully circumferential endoscopic full thickness resection (eFTR), tissue closure and/or tissue apposition.

BACKGROUND

Endoscopic mucosal resection (EMR) and/or endoscopic submucosal dissection (ESD) procedures may be used to remove benign or diseased tissue, e.g., lesions, cancerous tumors, and/or other anomalies, from a patient's gastrointestinal system. In some patients, full thickness resection (FTR), which may be partially or fully circumferential in a body lumen, may be necessary to ensure complete removal of the diseased tissue, as opposed to removal of only the mucosal layers of the gastrointestinal system.

However, FTR procedures may pose additional challenges such as anatomical difficulties of removing tissue adjacent critical internal organs and other sensitive structures, as well as risk of post-operative leakage, potentially increasing a patient's health risk in undergoing an FTR procedure.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a device for tissue resection from within a body lumen may include an elongate body having a cavity at a distal end, and a tissue retractor extendable distally from the distal end of the elongate body and including an expansion mechanism. The expansion mechanism may include a plurality of arms each having a first end coupled around a distal cap and expandable radially outward from the distal cap, such that an anchoring mechanism on a second end of the arms may be engageable with selected tissue for resection of the body lumen. The device may further include a tissue resecting device.

In various of the foregoing and other embodiments of the present disclosure, the tissue resection device may further include a sheath attached to the tissue retractor and extendable from the elongate body. The expansion mechanism may further include a plurality of connectors each having a first end coupled to the sheath and a second end coupled to a respective arm. The expansion mechanism may be configured to radially expand symmetrically around the distal cap and the sheath. The expansion mechanism may be configured to radially expand asymmetrically around the distal cap and the sheath. The tissue closure device may be disposed on an outer surface of the distal end of the elongate body. The tissue retractor may be configured to extend through a wall of the body lumen, the plurality of arms positioned substantially parallel to the elongate body, and engage the selected tissue for resection when the plurality of arms is expanded radially. The tissue resecting device may be an internal shear edge of the cavity, a shear proximal edge of the distal cap, or a shear edge of a distal end of the elongate body, or combinations thereof. The tissue resecting device may be a mechanical cutting tool or a cauterizing tool, or combinations thereof.

According to an exemplary embodiment of the present disclosure, a system for tissue resection from within a body lumen may include a lumen extendable into a patient. The lumen may include one or more working channels for delivering accessories to selected tissue for resection of the body lumen. The system may further include a tissue resection device deliverable over the lumen. The tissue resection device may include an elongate body having a cavity at a distal end. The tissue resection device may further include a tissue retractor extendable distally from the distal end of the elongate body, and may include an expansion mechanism. The expansion mechanism may include a plurality of arms each having a first end coupled circumferentially around a distal cap and expandable radially outward from the distal cap, such that an anchoring mechanism on a second end of each arm may be engageable with the selected tissue for resection of the body lumen. The tissue resection device may further include a tissue resecting device.

In various of the foregoing and other embodiments of the present disclosure, the tissue retractor may be configured to extend through the selected tissue for resection to an outer surface of the body lumen. The plurality of arms may be positioned substantially parallel to the elongate body, and may engage with the outer surface when the plurality of arms is expanded radially. The tissue retractor may be configured to retract the arms substantially parallel to the elongate body while the anchoring mechanisms are engaged with the outer surface of the selected tissue for resection. The tissue retractor may be configured to retract proximally towards the elongate body such that the arms are receivable in the cavity. The tissue resection system may further include a sheath attached to the tissue retractor and extendable from the elongate body. The sheath and the lumen may be coaxial such that the sheath may be extendable and retractable with respect to the elongate body along the lumen.

According to an exemplary embodiment of the present disclosure, a method for resection of selected tissue in a body lumen of a patient may include positioning a distal end of a lumen in the body lumen of the patient to the selected tissue for resection, and extending a tissue resection device to the selected tissue for resection. The tissue resection device may include an elongate body having a cavity at a distal end and a tissue retractor extendable distally from the distal end of the elongate body. The method may further include advancing the tissue retractor from an inner surface of the selected tissue to an outer surface of the selected tissue. The method may further include radially expanding a plurality of arms on an expansion mechanism of the tissue retractor, and engaging an anchoring mechanism on each arm to the tissue selected for resection. The method may further include retracting the plurality of arms radially inward while the anchoring mechanisms are engaged to the selected tissue for resection, to capture the selected tissue. The method may further include retracting the tissue retractor in proximally toward the elongate body such that the captured tissue is received within the cavity of the elongate body, and resecting the selected tissue from the body lumen.

In various of the foregoing and other embodiments of the present disclosure, the method may further include piercing the inner surface of the selected tissue by an accessory delivered by the lumen and extending the lumen through an opening to the outer surface of the selected tissue. The method may further include resecting the selected tissue by an internal shear edge of the cavity, a shear proximal edge of the distal cap, or a shear edge of a distal end of the elongate body, or combinations thereof. The expansion mechanism may further include a plurality of connectors each having a first end coupled to a sheath distally extendable from the elongate body, and a second end may be coupled to a respective arm, such that the plurality of arms may be radially expandable by articulation of the connectors. The method may further include closing remaining tissue of the body lumen by a tissue closure device, and the tissue closure device may be disposed on an outer surface of the distal end of the elongate body.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 2A-2B illustrate an exemplary embodiment of a tissue resection device in accordance with the present disclosure;

FIGS. 3A-3C illustrate exemplary embodiments of a tissue retractor of a tissue resection device in accordance with the present disclosure;

FIGS. 4A-4G illustrate an exemplary tissue resection system and process for tissue resection in accordance with the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

It may be understood that references to "proximal" may be defined as an end of the systems and devices closest to the entry point of the patient and "distal" may be defined as an end of the systems and devices closest to the desired location of the system and devices in the patient (e.g., a patient's gastrointestinal system).

Figure 1:
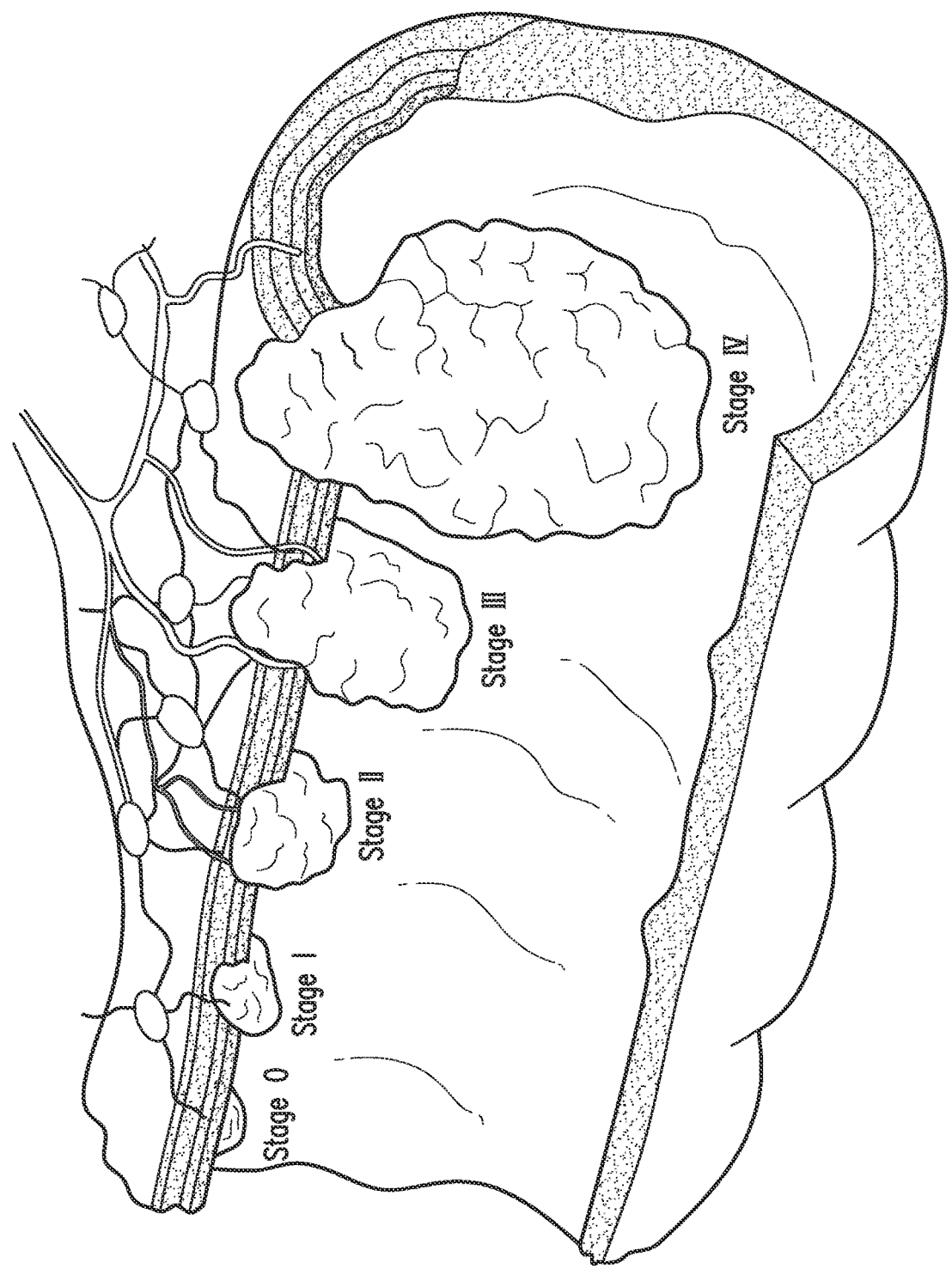
FIG. 1 illustrates a body lumen of a patient.

As described above, patients with diseased or other tissue in the gastrointestinal system may require resection. Referring to FIG. 1, various sized lesions are illustrated in a body lumen (e.g., gastrointestinal system) of a patient. As shown, earlier stages of diseased tissue may not extend through all the layers of the body lumen, which may allow for resection of only the affected tissue layers. However, as diseased tissue advances to later stages, resection of the entire tissue portion (e.g., full thickness resection) may be needed to fully excise the diseased tissue from the patient. Exemplary embodiments of devices, systems, and methods for partial or full thickness tissue resection in accordance with the present disclosure may allow for a selected tissue section containing diseased tissue to be contained and resected from surrounding tissue, the surrounding tissue then being joined together to close a gap formed by the resection of the selected tissue. In some embodiments, the tissue resection may be fully circumferential, e.g., extending 360° around a body lumen. In other embodiments, the tissue resection may be partially circumferential, e.g., extending less than 360° around a body lumen. Although "resection" is used throughout the disclosure, exemplary embodiments of the present disclosure may encompass resecting, dissecting, removing, ablating, cutting vaporizing, freezing, etc., and may be full thickness, partial thickness, and in instances of a procedure occurring in a body lumen, may be partial and/or fully circumferential.

According to exemplary embodiments of the present disclosure, an expandable device may be delivered from within a body lumen through a wall of the body lumen, e.g., to an outer surface of a body lumen, for capturing a selected tissue for resection in the device. It is understood that the device may be utilized in partial and/or full circumferential full thickness resection procedures. It is understood that selected tissue for resection may be an area of diseased tissue, e.g., including tumors and/or lesions, as well as a portion of healthy tissue immediately adjacent the diseased tissue. A portion of healthy tissue may be resected to minimize a risk of not fully capturing the diseased tissue and/or dislodging diseased tissue cells to potentially contaminate another tissue region. In some embodiments, the selected tissue for resection may include a benign cyst or legion. Although the body lumen is described with respect to the gastrointestinal system, including but not limited to an intestine, colon, and/or duodenum, it is understood that exemplary embodiments of devices, systems, and methods of the present disclosure may apply to any body lumen in a patient. In some embodiments, the selected tissue may be in a body lumen such as an intestine, colon, and/or other gastrointestinal system. The resection system may be configured for full thickness resection of a large intestine, although it is envisioned that the resection device may be configured for other anatomical resecting as well.

Referring now to FIGS. 2A-2B, an exemplary embodiment of a device 200 in accordance with the present disclosure is illustrated. The device 200 may be configured to extend along an axis 202 and may have a proximal end 200a and a distal end 200b. The device 200 may include an elongate body 205 having a proximal end 205a and a distal end 205b. The body 205 may be substantially cylindrical and may extend along the axis 202. The device 200 may include a handle 210 having a proximal end 210a and a distal end 210b, the distal end 210b of the handle 210 being coupleable to the proximal end 205a of the body 205. The body 205 may include a cavity 215 for capturing and/or receiving resected tissue 220, and/or receiving at least a portion of a tissue retractor 230.

A lumen 225 may be extendable through the body 205 along the axis 202, and may be configured to extend through the selected tissue for resection 220, e.g., the lumen 225 may be extendable from an inner surface 220a of the tissue 220 to an outer surface 220b of the tissue 220 in a distal direction along the axis 202. The lumen 225 may have one or more working channels for additional accessories to be used at the site of the selected tissue for resection, and in some embodiments may be a Boston Scientific SpyScope™ catheter. A tissue retractor 230 may be disposed distally of the cavity 215 and may be deliverable through the selected tissue for resection 220, e.g., to the outer surface 220b of the tissue 220. A tissue closure device 235 may be disposed on an outer surface 240 of the body 205. In some embodiments, the tissue closure device 235 may be one or more clips, clamps, bands, rings, sutures, and/or other mechanical fastener to close the tissue after resection.

The tissue retractor 230 may be releasably attachable to the cavity 215 by a sheath 245 along the axis 202, to extend the tissue retractor 230 in a distal direction along the axis 202 to the outer surface 220b of the selected tissue for resection 220 separate from the cavity 215. For example, the cavity 215 may remain inside the body lumen while the tissue retractor 230 is extendable to the outside of the body lumen. The sheath 245 may be coaxial to the lumen 225, so that the tissue retractor 230 may be retractable in a proximal direction along the axis 202 to capture the selected tissue for resection 220, at least a portion of the tissue retractor 230 and the selected tissue for resection 220 being retractable into the cavity 215. The sheath 245 may be attached to the handle 210 for manipulation of the tissue retractor 230 by a medical professional. For example, a handle 210 may have controls for axially extending the tissue retractor 230 and independently opening and/or closing the tissue retractor 230.

Figure 3A:
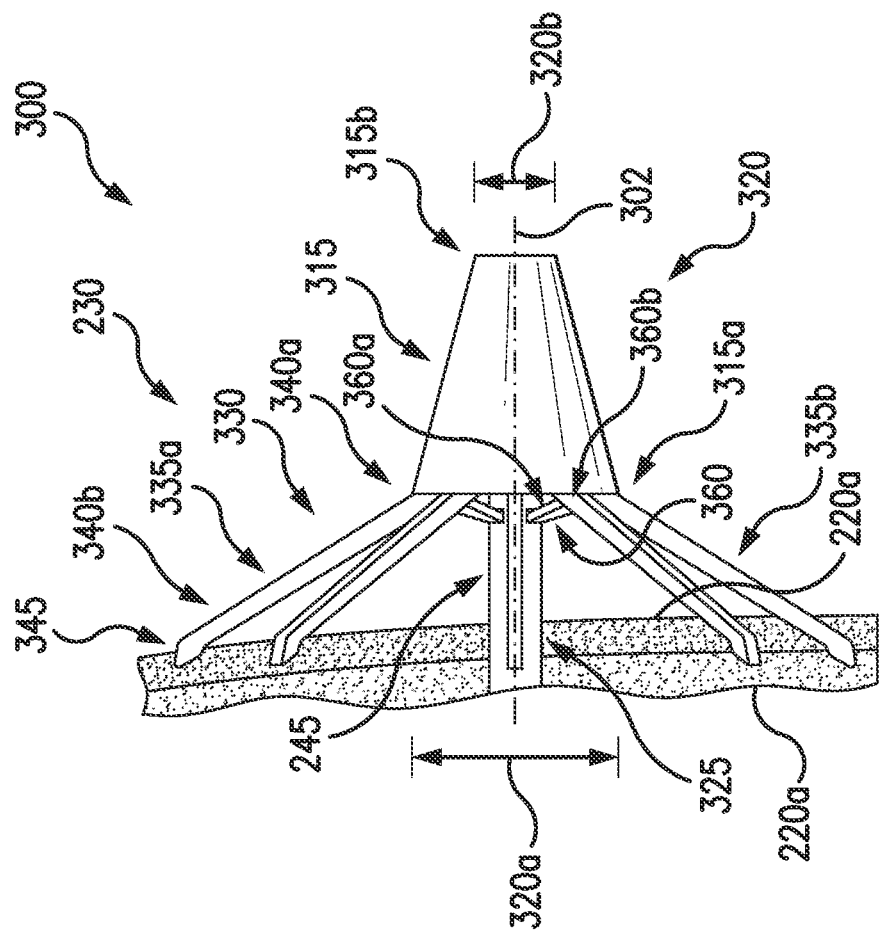
Figure 3D:
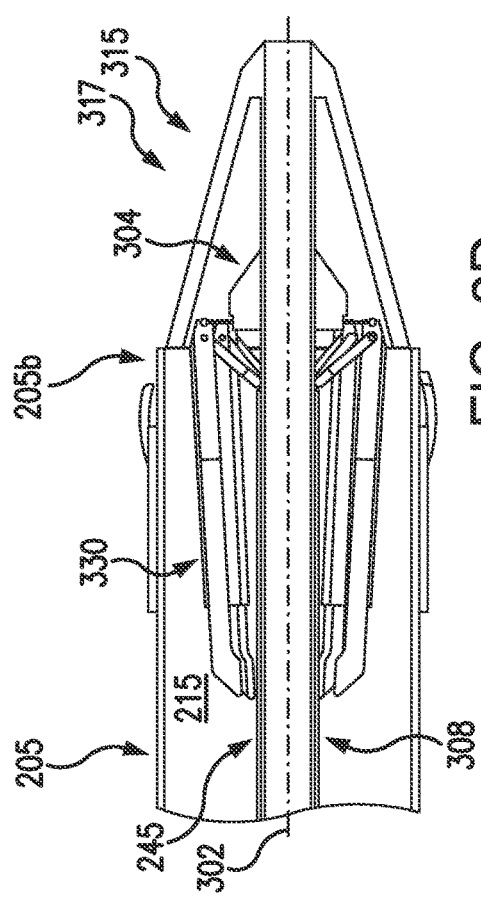
FIGS. 3D-3E illustrate sectional views of an exemplary embodiment of a tissue retractor of a tissue resection device in an open position and a closed position in accordance with the present disclosure.

Referring now to FIGS. 3A-3J, exemplary embodiments of a tissue retractor are illustrated in accordance with the present disclosure. FIGS. 3A-3C, and 3E illustrate exemplary embodiments of the tissue retractor 230 in an extended position 300, 300' and a retracted position 305, e.g., during deployment in a body lumen. FIG. 3D illustrates an exemplary embodiment of the tissue retractor 230 in a closed position, e.g., prior to deployment in a body lumen. As described above, the tissue retractor 230 may be attached to the sheath 245 for extending through the selected tissue for resection 220 and retracting back to the cavity 215 of the body 205. In some embodiments, the tissue retractor 230 may include a distal cap 315, attachable at the distal end 205b of the body 205. The distal cap 315 may be coaxial to the sheath 245, e.g., along axis 302. The distal cap 315 may be a frustoconical shape, e.g., having a tapered outer surface 320, so that the distal cap 315 may have a smaller diameter 320b at the distal end 315b of the distal cap 315 and a larger diameter 320a at the proximal end 315a of the distal cap 315. A frustoconical shape may be advantageous for extending the tissue retractor 230 through the tissue 220. For example, the smaller diameter 320b may be inserted in the tissue 220 after a tissue penetration device penetrates the tissue to create an opening 325, so that the opening 325 conforms to the tapered outer surface 320 of the distal cap 315 as it is passed through the opening 325. It is also understood that the distal end 315b of the distal cap 315 may have a sharp edge for penetrating (e.g., cutting) through the tissue 220.

Figure 3E:
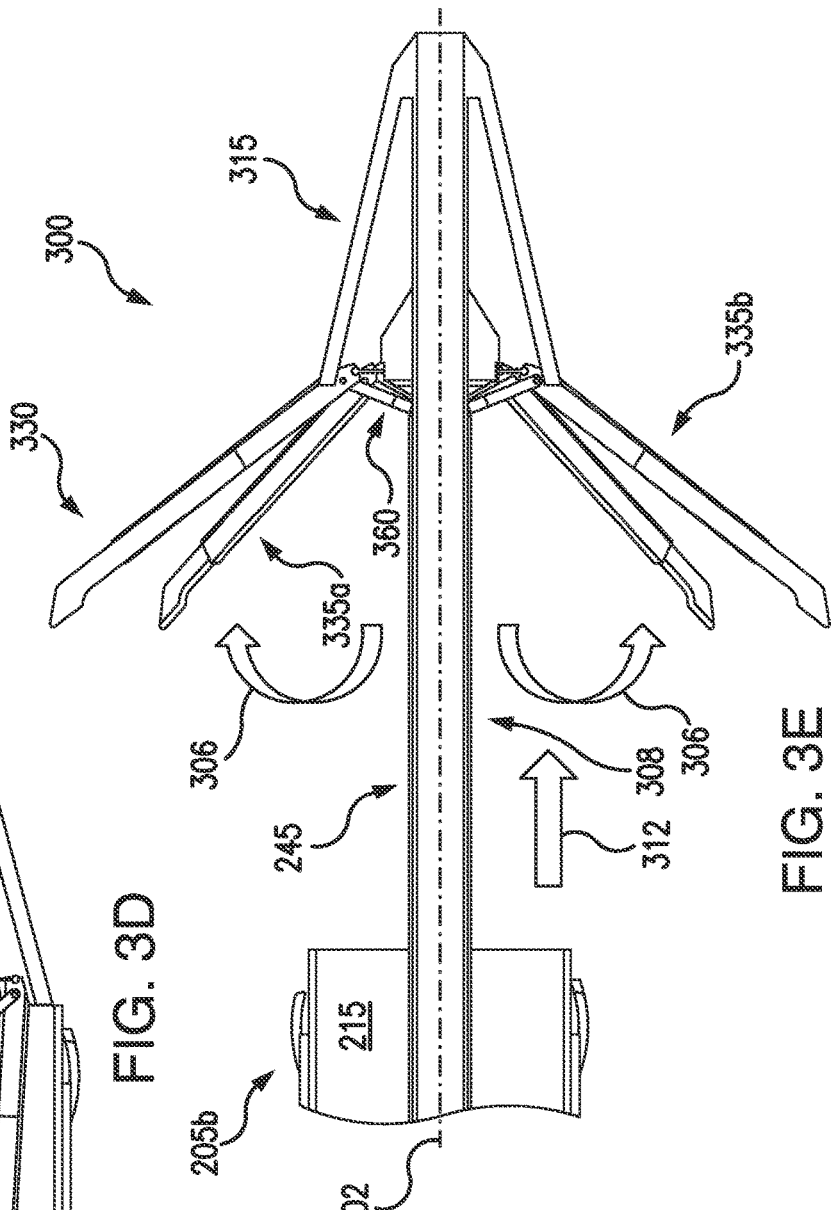

As shown in FIGS. 3D-3E, the distal cap 315 may be substantially hollow, for receiving at least a portion of an expansion mechanism 330, 330'. The expansion mechanism 330 may include a plurality of arms 335, e.g., 335a, 335b, . . . 335n, for extension on the outer surface 220b of the selected tissue for resection 220. It is understood that any number "n" of arms 335 may be included in the tissue retractor 230. The arms 335 may be coupled circumferentially around a hub 304, e.g., disposed internally at the proximal end 315b of the distal cap 315. In some embodiments, the arms 335 may be coupled to allow movement, including but not limited to rotational, pivoting, telescoping, and/or twisting movement. For example, the arms 335 may be hingedly, pivotably, and/or otherwise rotatably coupled to the hub 304. The arms 335 may have a first end 340a and a second end 340b, the first end 340a being coupled to the hub 304, and the second end 340b contactable with the outer surface 220b of the selected tissue for resection 220. In some embodiments, the second end 340b may include an anchoring mechanism 345 to engage (e.g., grasp) the selected tissue for resection 220. In embodiments, the anchoring mechanism 345 may be a hook, barb, clip, clamp, and the like.

The arms 335 may be radially expandable from the distal cap 315 and/or the sheath 245. Each arm 335a, 335b, . . . 335n may be articulatable independently of each other and/or may all be articulatable as a group. In some embodiments, as shown in FIG. 3A, the arms 335 may be radially expandable symmetrically around the sheath 245 and/or the distal cap 315. For example, the selected tissue for resection 220 may be symmetrically surrounding the sheath 245 and/or the distal cap 315. In other embodiments, as illustrated in FIG. 3B, arms 335' may be radially expandable asymmetrically from the distal cap 315. The arms 335, 335' may be configured of differing lengths, may be telescopic and/or foldable for adjusting to a selected length, so the expansion mechanism 330, 330' may be configured to extend or expand each arm 335'a, 335'b, . . . 335'n independently of each other to the selected length. This may be advantageous when it is desired to extend the tissue retractor 230 through the tissue 220 proximate to a lesion, cyst, tumor, or other diseased tissue 350 without disturbing and/or dislodging the diseased tissue cells. The selected tissue for resection 220 may extend asymmetrically around the tissue retractor 230. As such, an asymmetrical expansion mechanism 330' may be advantageous for the anchor mechanism at the second end 340b of the arms 335 to engage to a portion of healthy tissue 355 surrounding the diseased tissue 350 (e.g., comprising a selected tissue for resection).

The expansion mechanism 330, 330' may further include connectors 360 attached to the first end 340a of the arms 335, 335', the sheath 245 and/or the hub 304 (see FIGS. 3D-3H). For example, the connectors 360 may be coupled to the sheath 245 at a first end 340a and the distal cap 315 and/or the arms 335, 335' at a second end 360b. The connectors 360 may be hingedly or rotatably attached to the distal cap 315, e.g., circumferentially around the proximal end 315a of the distal cap 315, so the arms 335, 335' may be expandable radially (e.g., in a direction illustrated by arrows 306) from the distal cap 315 and/or the sheath 245. In some embodiments, additional connectors 365 (see FIG. 3H) may be coupled between the hub 304 and the first end of the arm 340a, and a connector 360 may be coupled between the first end of the arm 340a and a shaft 308. The connector 360 and additional connectors 365 may be articulatable independently of each other, e.g., the arms 335 may be articulatable about an axis 360a, which may be a connection between the connector and the first end of the arm 340a, and an axis 365a, which may be a connection between the additional connector 365 and the first end of the arm 340a. In some embodiments, the connector 360 may also be hingedly or rotatably coupled to the shaft 308, e.g., about an axis 308a. In some embodiments, the additional connector 365 may be coupled to the hub 304, either fixedly, or hingedly or rotatably. The connectors 360 may articulate the arms 335, 335' to an extended and/or retracted position, e.g., similar to an umbrella. In some embodiments, the expansion mechanism 330, 330' may be operable by a coaxial shaft 308, in which the connectors 360 are coupled (e.g., hingedly or rotatably) for manipulating between an extended and retracted position. For example, a medical professional may manipulate a proximal end of the shaft 308 (e.g., external to a patient), to extend and/or retract the expansion mechanism 330, 330'.

The expansion mechanism 330, 330' may articulate the connectors 360 and the arms 335, 335', e.g., relative to the sheath 245, shaft 308, hub 304, and/or the distal cap 315, to an extended position 300, 300' as shown in FIGS. 3A-3B, 3E, and 3G. When the anchoring mechanisms 345 engage the outer surface 220b of the selected tissue for resection 220, the expansion mechanism 330, 330' may articulate the connectors 360 and/or the additional connectors 365 via the shaft 308 and hub 304 for manipulating the arms 335, 335', e.g., relative to the sheath 245, shaft 308, hub 304, and/or the distal cap 315, to a retracted position 305 as shown in FIG. 3C, 3F, and/or in a closed position 317 as shown in FIG. 3D. In the retracted position 305, the selected tissue for resection 220 may be capturable between the arms 335, 335' by retracting the arms to a radially inward position. The retracted position 305 may have the arms 335, 335' substantially parallel to the sheath 245 along the axis 302, so that the selected tissue for resection 220 is captured between the arms 335, 335' and the sheath 245 and shaft 308. The expansion mechanism 330, 330' may also be in a retracted position 305 when extending out of the cavity 215, e.g., for positioning through the tissue. For example, the sheath 245, shaft 308, expansion mechanism 330, 330', and distal cap 315 may be extendable along the axis 302 in a distal direction as indicated by arrow 312 (see FIG. 3E). In the closed position 317, the arms 335, 335' may also be substantially parallel to the sheath 245 along the axis 302 to fit within the cavity 215.

Figure 3G:
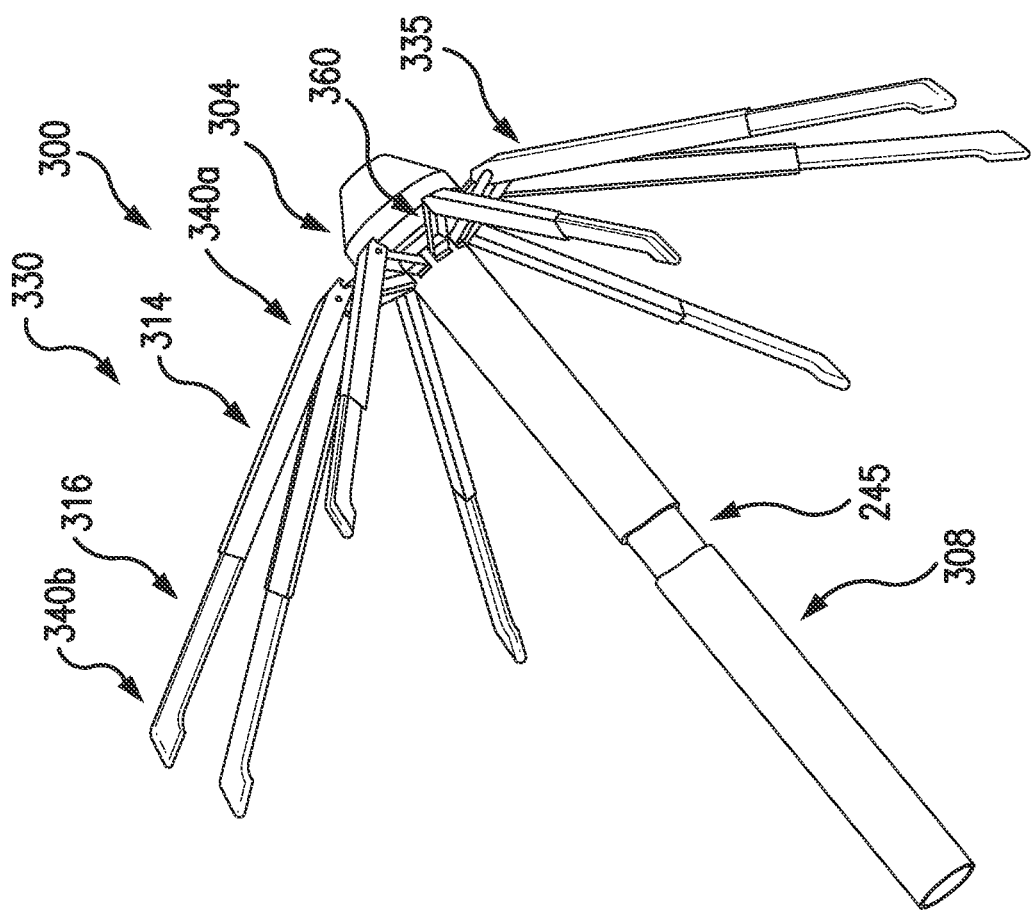
FIGS. 3F-3G illustrate perspective views of an exemplary embodiment of a tissue retractor of a tissue resection device in an open position and a closed position in accordance with the present disclosure.
Figure 3F:
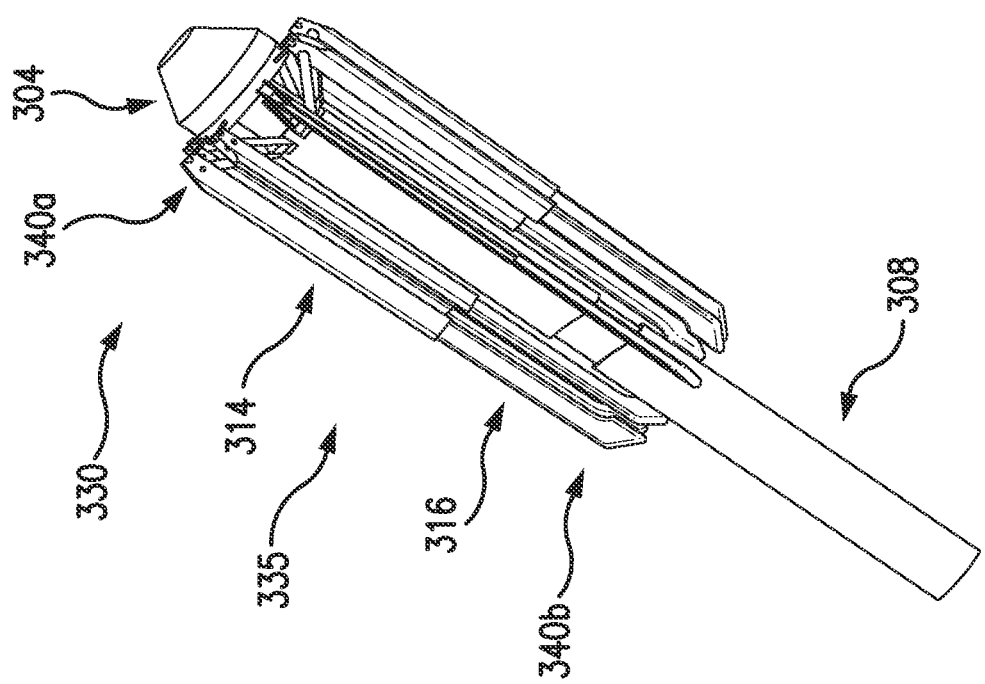
Figure 3H:
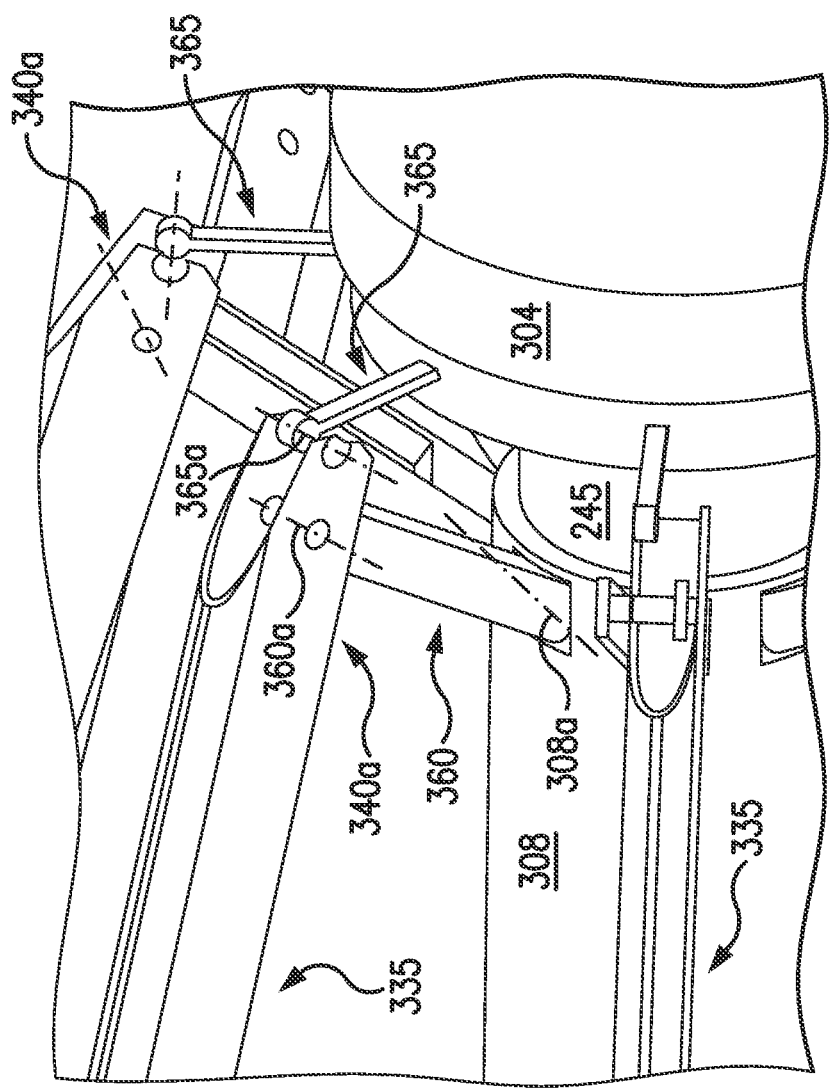
FIG. 3H illustrates an exemplary embodiment of connectors of a tissue retractor of a tissue resection device in accordance with the present disclosure.

As shown in FIGS. 3F-3G, and as described above, the arms 335 (e.g., 335a, 335b, . . . 335n) may be adjustable, e.g., telescoping. For example, a length of the arm 335 between the first end 340a of the arm and the second end 340b of the arm may be variable. The arms 335 may be adjustable to accommodate different amounts of selected tissue for resection, and/or capturing desired areas of tissue. The arms 335 may have a first portion 314 and a second portion 316. The second portion 316 may be adjustable relative to the first portion 314, e.g., the second portion 316 may telescope from the first portion 314. Adjustable arms 335 may allow for symmetrical or asymmetrical positioning of the expansion mechanism for capturing the selected tissue.

Figure 3I:
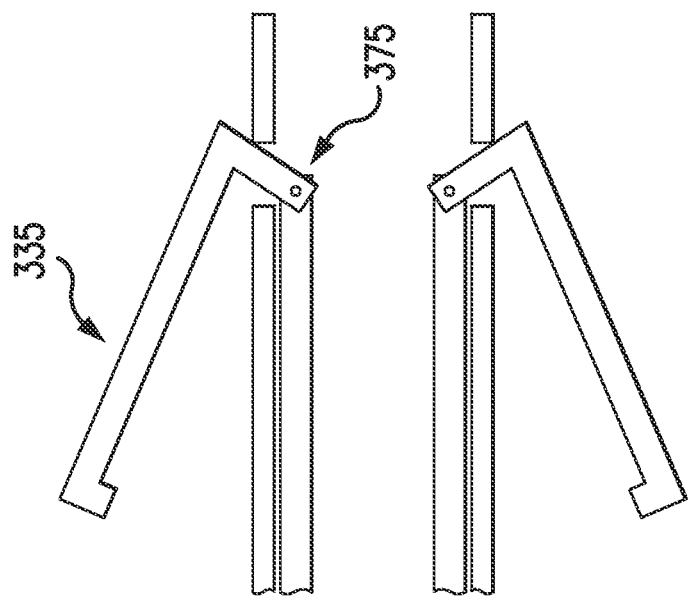
FIGS. 3I-3J illustrate exemplary embodiments of a tissue retractor of a tissue resection device in an open position and a closed position in accordance with the present disclosure.
Figure 3I:
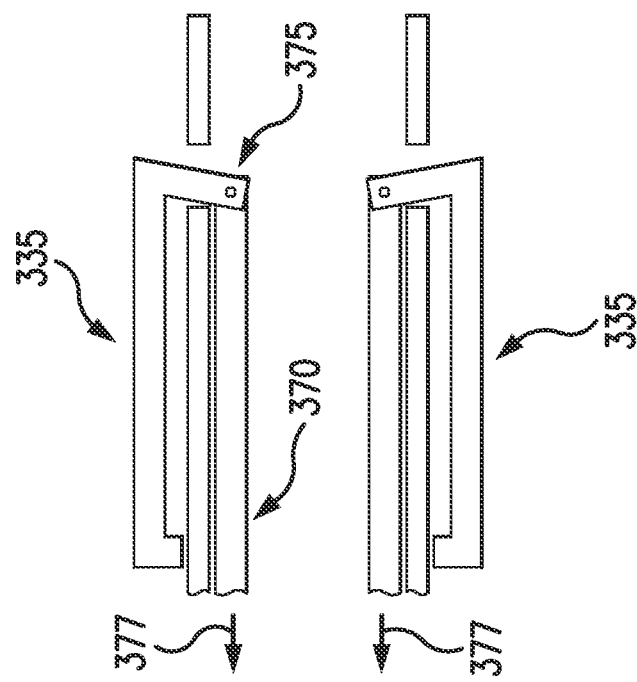
Figure 3J:
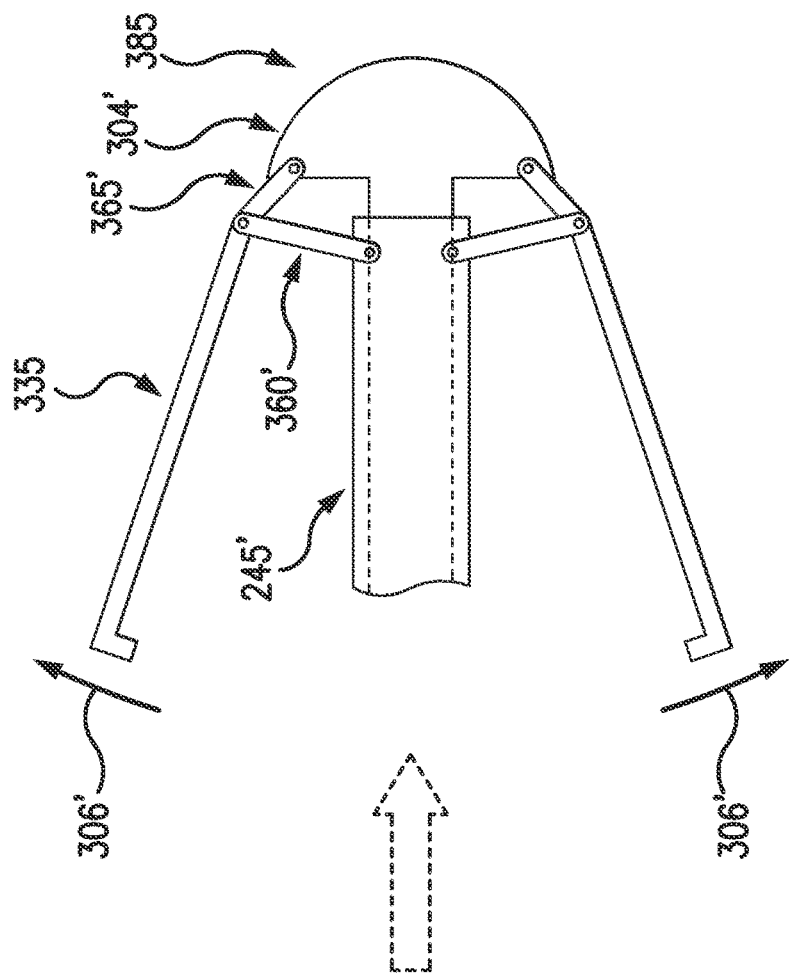
Figure 3J:
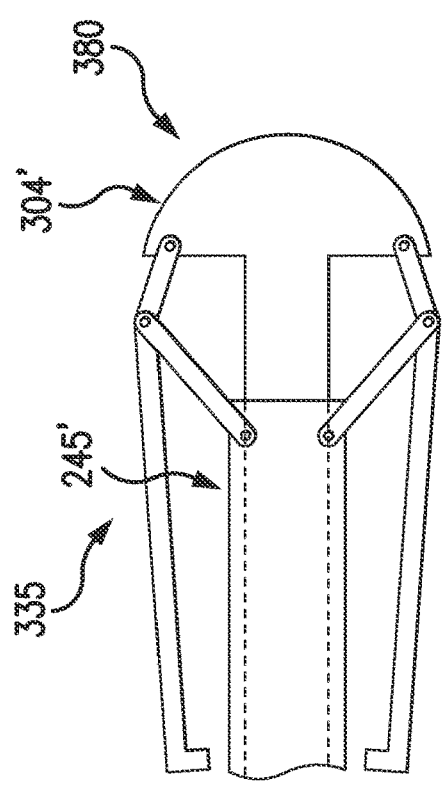

FIGS. 3I-3J illustrate other exemplary embodiments of an expansion mechanism in accordance with the present disclosure. As shown in FIG. 3I, arms 335 may be connected to a pullwire 370, e.g., at a connection 375. The pullwire 370 may extend to the proximal end of the device, e.g., external to the patient for manipulation by a medical professional. When the pullwire 370 is pulled in a proximal direction (e.g., in a direction indicated by arrows 377), for example, the arms 335 may articulate to an extended position relative to the sheath 245. As shown in FIG. 3J, a sheath 245' may be movable relative to a hub 304'. In some embodiments, at least a portion of the hub 304' may be receivable within a portion of the sheath 245'. The arms 335 may be coupled to a connector 360' and/or an additional connector 365', where the connector 360' may be also coupled to the sheath 245' and the additional connector 365' may be also coupled to the hub 304'. As described above, the connector 360' and additional connector 365' may be hingedly or rotatably coupled to the arms 335, sheath 245', and/or hub 304'. In a retracted position, the hub 304' may be disposed in a first position 380 relative to the sheath 245'. When the medical professional articulates the sheath 245', at least a portion of the hub 304' may be received within the sheath 245' to a second position 385, resulting in an extension of the arms 335 via the connectors 360' and additional connectors 365'. For example, the arms 335 may be rotatable in a direction indicated by arrows 306'. It may be understood that the connectors 360' and additional connectors 365' may be operable in a manner similar to the connectors 360 and additional connectors 365 (see FIG. 3H).

Figure 4A:
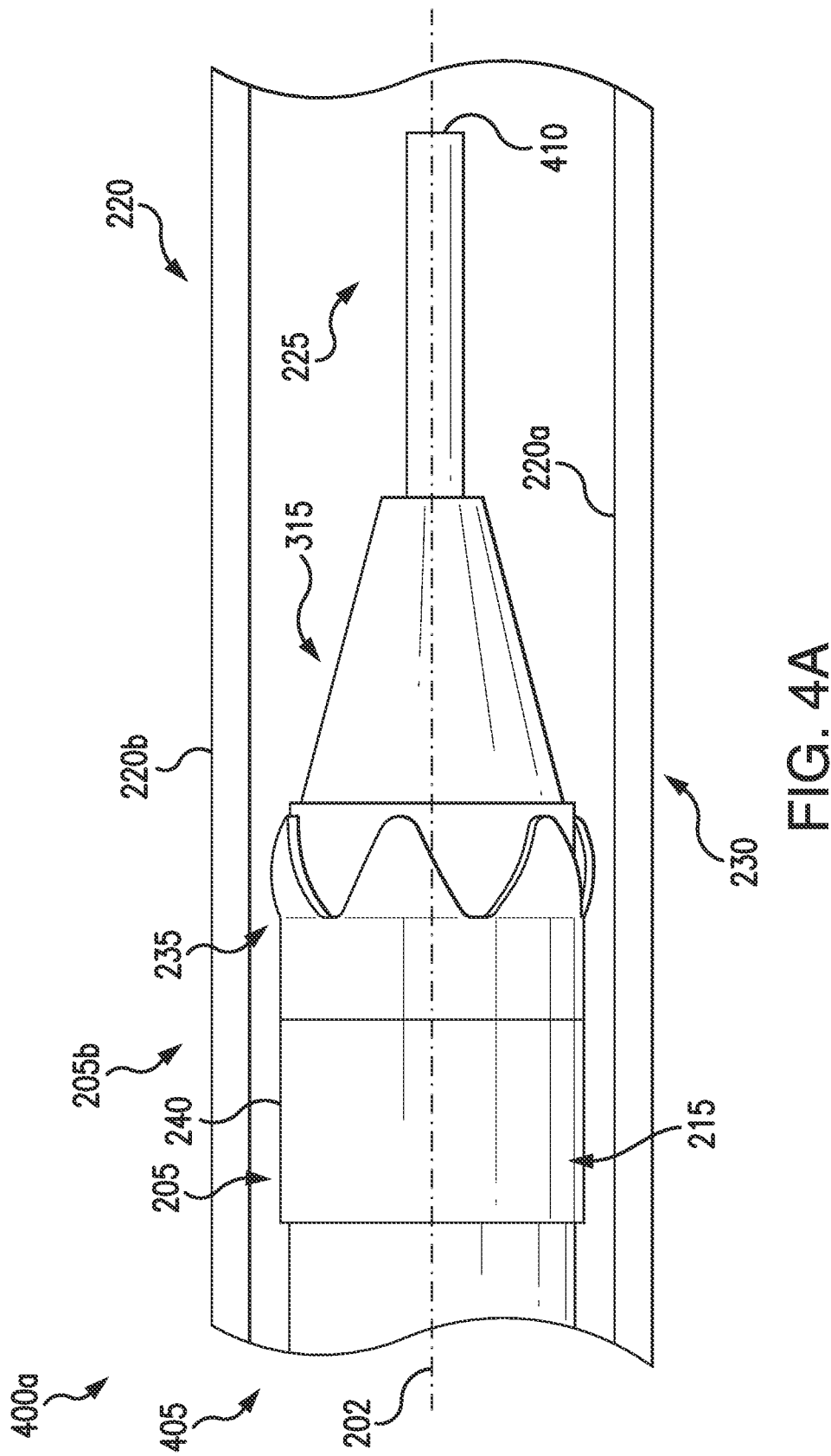

Referring now to FIGS. 4A-4G, a process for tissue resection using an exemplary embodiment of a tissue resection system 405 in accordance with the present disclosure is shown. As shown in FIG. 4A at step 400a, the tissue resection system 405 may be extendable along an exterior surface 225a of a lumen 225, or a catheter, in a patient, e.g., in a body lumen of the patient, to a location of a selected tissue for resection. The distal end 205b of the body 205 may include the cavity 215 and the tissue retractor 230. When the system 405 is delivered to the targeted location of the selected tissue for resection 220, the expansion mechanism 330, 330' may be at least partially received within the cavity 215, so that the distal cap 315 is adjacent the cavity 215. In some embodiments, a tissue closure device 235 may be disposed on the outer surface 240 of the body 205.

Figure 5:
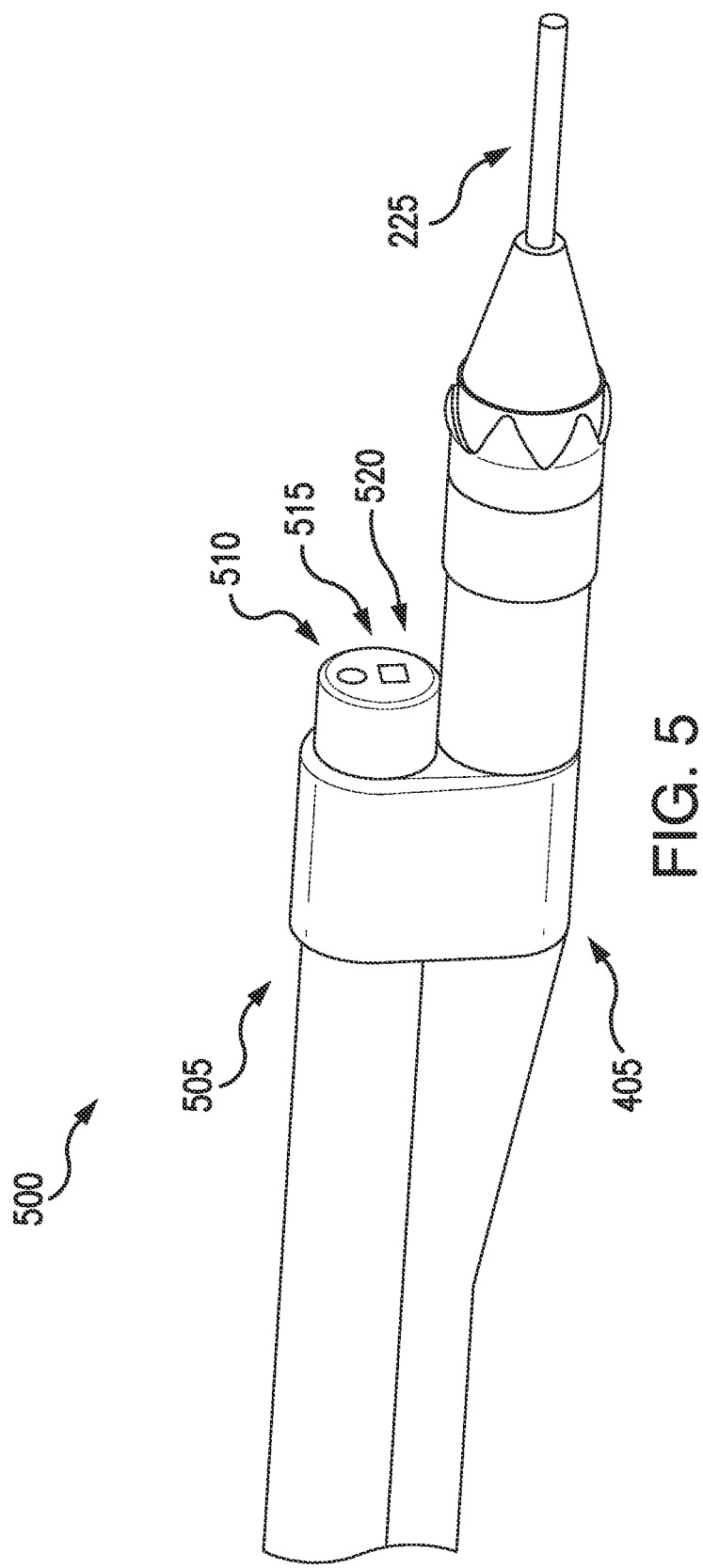
FIG. 5 illustrates an exemplary embodiment of a tissue resection device in accordance with the present disclosure.

The system 405 may be deliverable in the body lumen by a navigation and/or visualization device, which in some embodiments may be included in the lumen 225. The visualization device may be an optical wand, an integrated camera chip, an ultrasonic device, an endoscope (e.g., Spy- Scope™ catheter), and/or other known visualization techniques including but not limited to direct visualization, ultrasonic imaging, and/or fluoroscopy and/or radiopaque markers. The system 405 may have an independent steering system, although it is also envisioned that the system 405 may use a steerable device (e.g., guidewire technique) in the body lumen as a guide. In some embodiments, an imaging device may be included on a distal face 410 of the lumen 225, so that the tissue 220 may be visualized. In some embodiments, in addition or alternative to the distal face imaging device, the system 405 may be connectable substantially parallel and adjacent to another imaging device (see FIG. 5). For example, at least a portion of the system 405 may be attachable to additional device 505 in parallel, or substantially parallel, for delivery in the body lumen. The additional device 505 may be attachable by any known mechanisms, including but not limited to a clip, clamp, or other attachment mechanism or sleeve. The additional device 505 may include one or more imaging devices 510 and/or lighting devices 515 on a distal face 520. The additional device 505 may provide additional visualization and/or navigation for the medical professional. For example, the lumen 225 may provide visualization to an outer surface 220b of the selected tissue, and the additional device 505 may provide visualization to an inner surface 220a of the selected tissue. This may allow the medical professional to ensure correct positioning and capture with respect to the selected tissue 220.

Figure 4B:
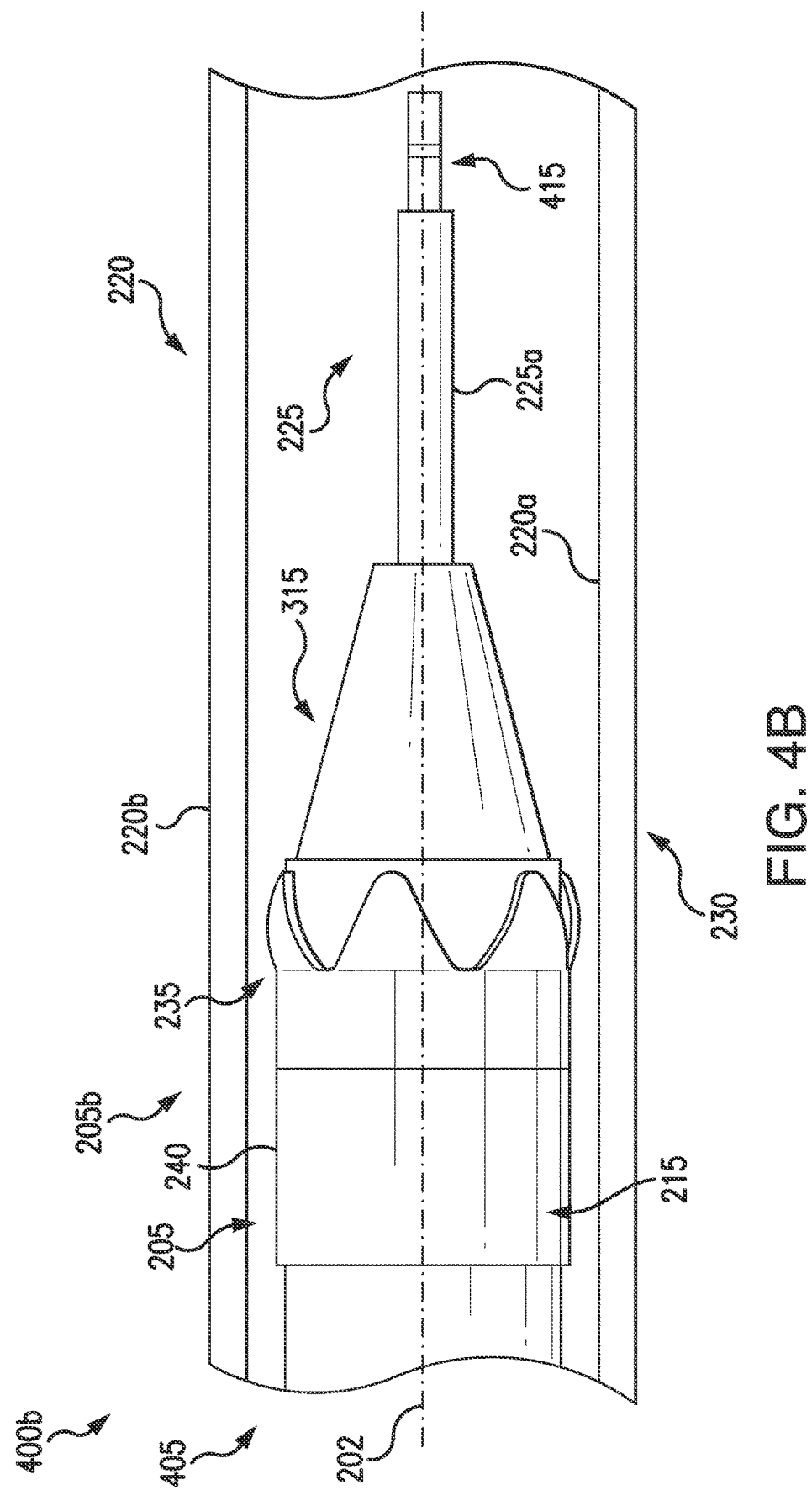
Figure 4C:
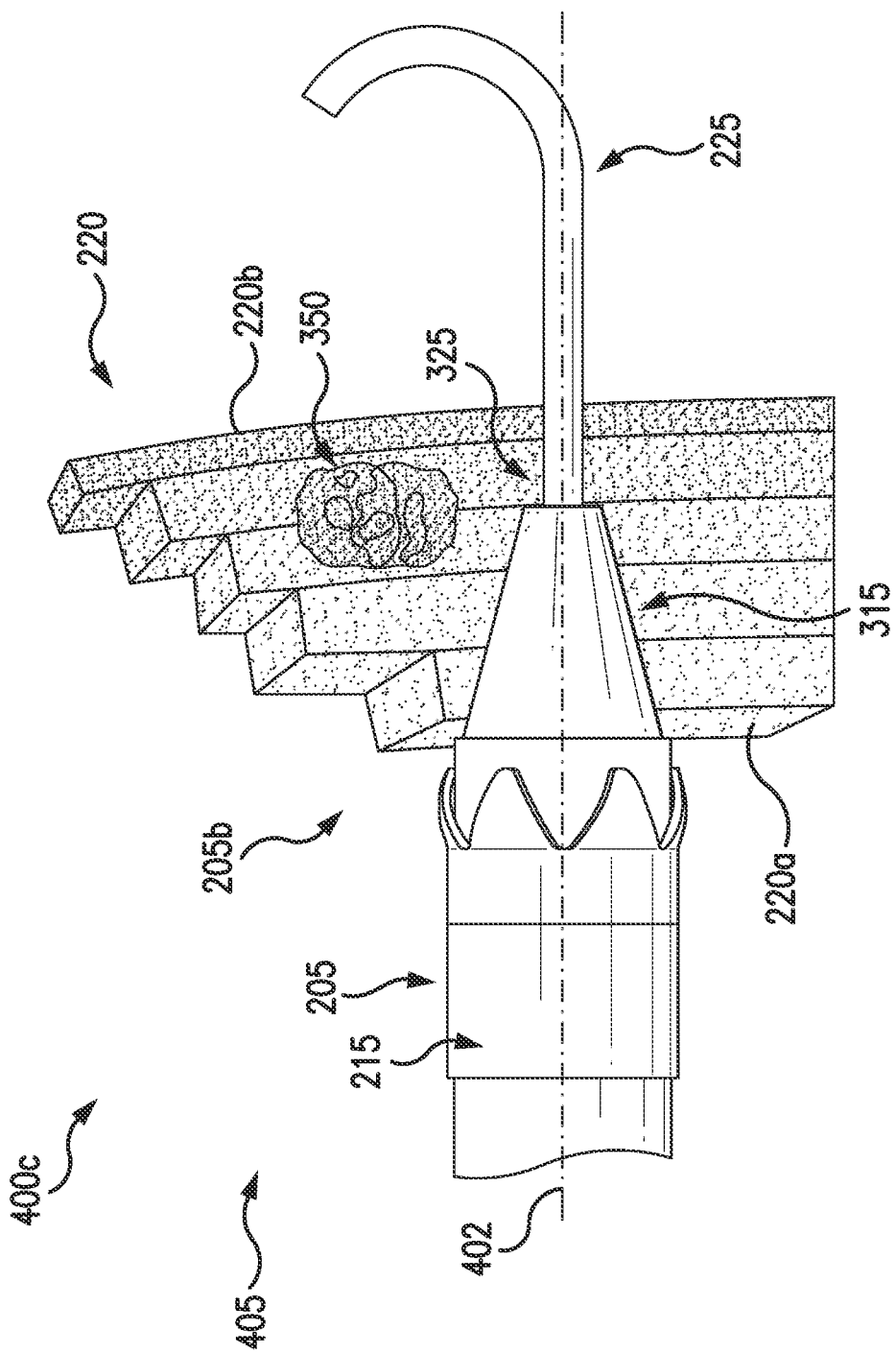

At step 400b as shown in FIG. 4B, a tissue penetrating device 415 may be extendable through the lumen 225, e.g., through a working channel, and may extend out the distal face 410 of the lumen 225. The tissue penetrating device may be extendable through a working channel of a visualization device, itself extendable through the lumen, e.g., so that penetration of the body lumen may be visualized as it is performed, such as a penetrating device extendable through a working channel of a Spyscope catheter. The tissue penetrating device 415 may be any tool for piercing, or penetrating tissue, such a knife, needle, blade, cautery, laser, and/or ultrasonic tool. The tissue penetrating device may be used to pierce through the selected tissue for resection 220, so that the lumen 225 and at least a portion of the system 405 may be extended to the outer surface 220b of the selected tissue 220, as shown in FIG. 4C at step 400c. In some embodiments, other accessories may be deliverable through the lumen 225, e.g., by one or more working channels, for use by the medical professional. For example, a fluid delivery device may deliver fluids (e.g., saline or CO2 gas) to insufflate an area outside of the body lumen. In some embodiments, adjacent lymph nodes may be examined and/or biopsied by grasping tools and collected by the lumen 225.

As described above, the tissue retractor 230 may be extendable in a distal direction along an axis 402 from the body 205 and advanced through the tissue 220 along the lumen 225 to create an opening 325. It is understood that the axis 402 may be substantially perpendicular to the body lumen (e.g., substantially perpendicular to axis 202) to extend transversely through the tissue 220. The lumen 225 may extend through the tissue 220 as it is pierced or penetrated, to maintain the opening 325. In some embodiments, the distal cap 315 may dilate the opening 325 by the frustoconical shape (e.g., the tapered outer surface 320) of the outer surface 320, so that the tissue retractor 230 may be advance through the tissue 220. In some embodiments, an independent dilation device may be used, including but not limited to a balloon and/or a blunt dissection tool for passage of the tissue retractor 230.

Figure 4D:
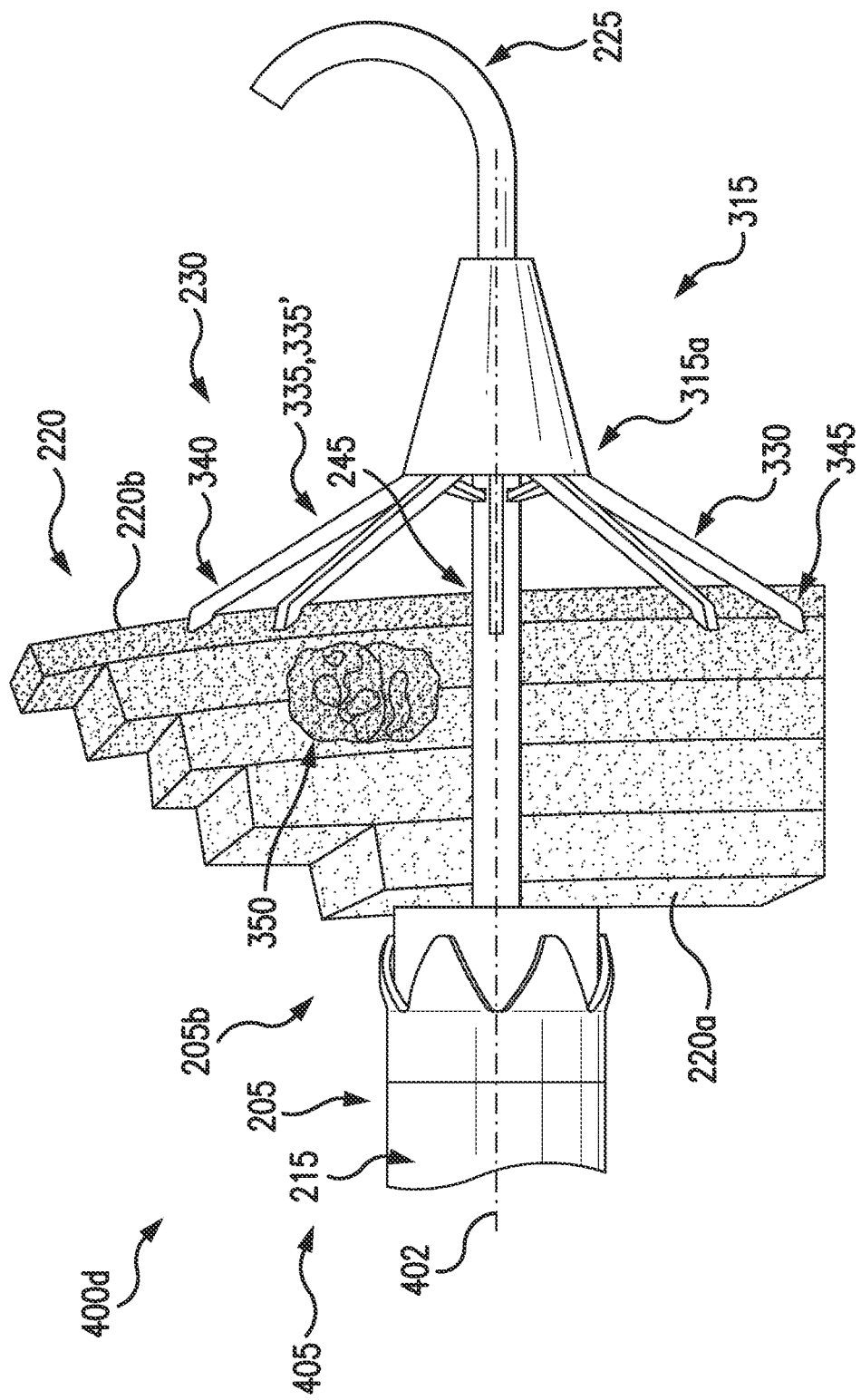

As shown in FIG. 4D, at step 400d, the tissue retractor 230 may be fully extended to the outer surface 220b of the selected tissue for resection 220 by the sheath 245. The arms 335, 335' may be deployable circumferentially around the proximal end 315a of the distal cap 315. As described above with respect to FIGS. 3A-3J, the arms 335, 335' may be deployable symmetrically and/or asymmetrically to surround the selected tissue for resection 220. For example, when the anchoring mechanism 345 on the second end 340b of the arms 335, 335' engages the selected tissue 220, a perimeter may be formed on the outer surface 220b to surround the selected tissue for resection 220. In some embodiments, the perimeter may be substantially circular, elliptical, and/or circumferential, but is understood that the perimeter may be any shaped formed by the second end 340b of the arms 335, 335'. As described above, the arms 335, 335' may be telescopic, and may be independently articulatable to form any shape radially around the distal cap 315 and/or the sheath 245.

Figure 4E:
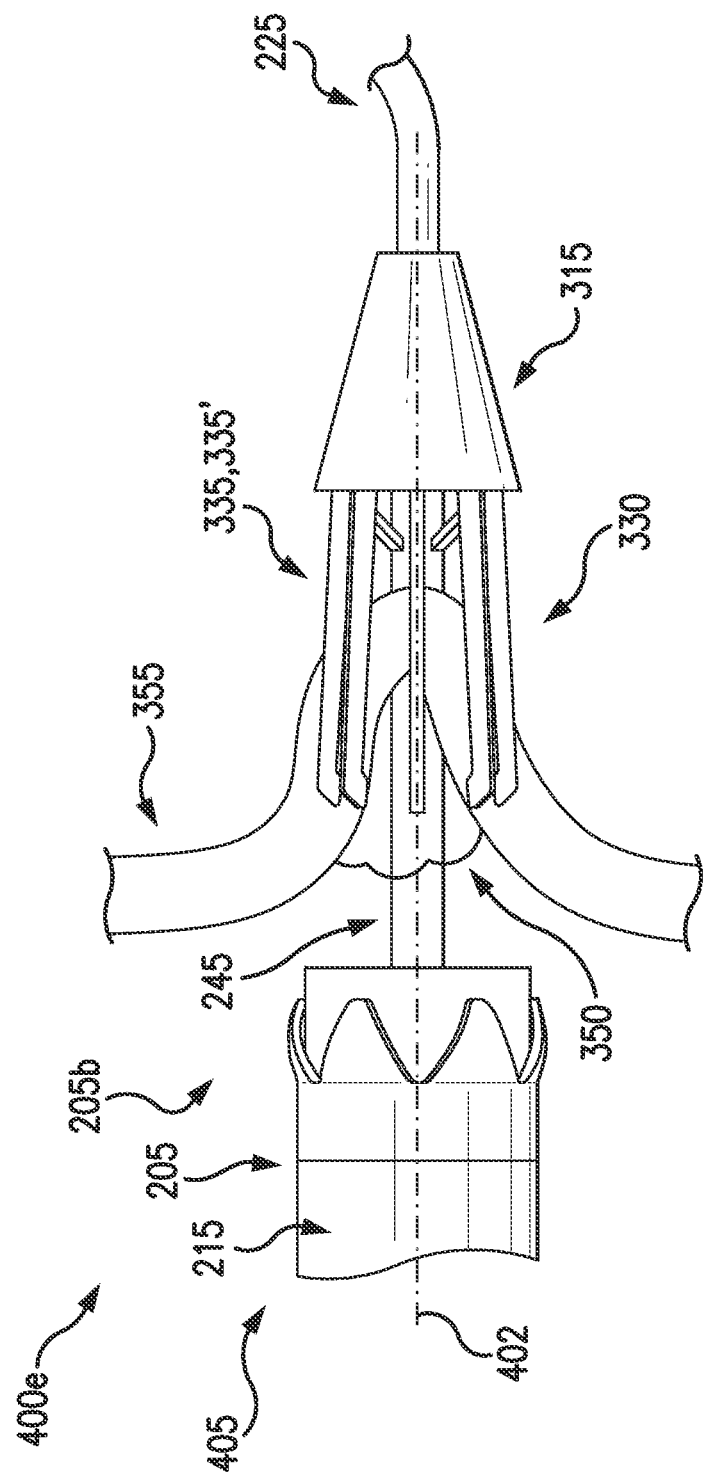

The anchoring mechanism 345 on each arm 335, 335' may engage (e.g., grasp or attach) to the outer surface 220b of the tissue selected for resection 220 without damaging the tissue. As shown in FIG. 4E, at step 400e, when the anchoring mechanism 345 of each arm 335, 335' are sufficiently engaged with the outer surface 220b of the tissue selected for resection 220, the arms 335, 335' may be retracted radially inward, gathering and capturing the selected tissue for resection 220 between the arms 335, 335' and the sheath 245. The selected tissue for resection 220 (for example, including a portion of healthy tissue 355 as well as a selected cyst, tumor, lesion, or other diseased tissue 350) may be captured by the tissue retractor 230 and may be moved in proximal direction along axis 402 towards the cavity 215 by the sheath 245. The tissue retractor with expansion mechanism may be extendable and/or retractable as needed to ensure all the selected tissue for resection is captured by the arms 335, 335'.

Figure 4F:
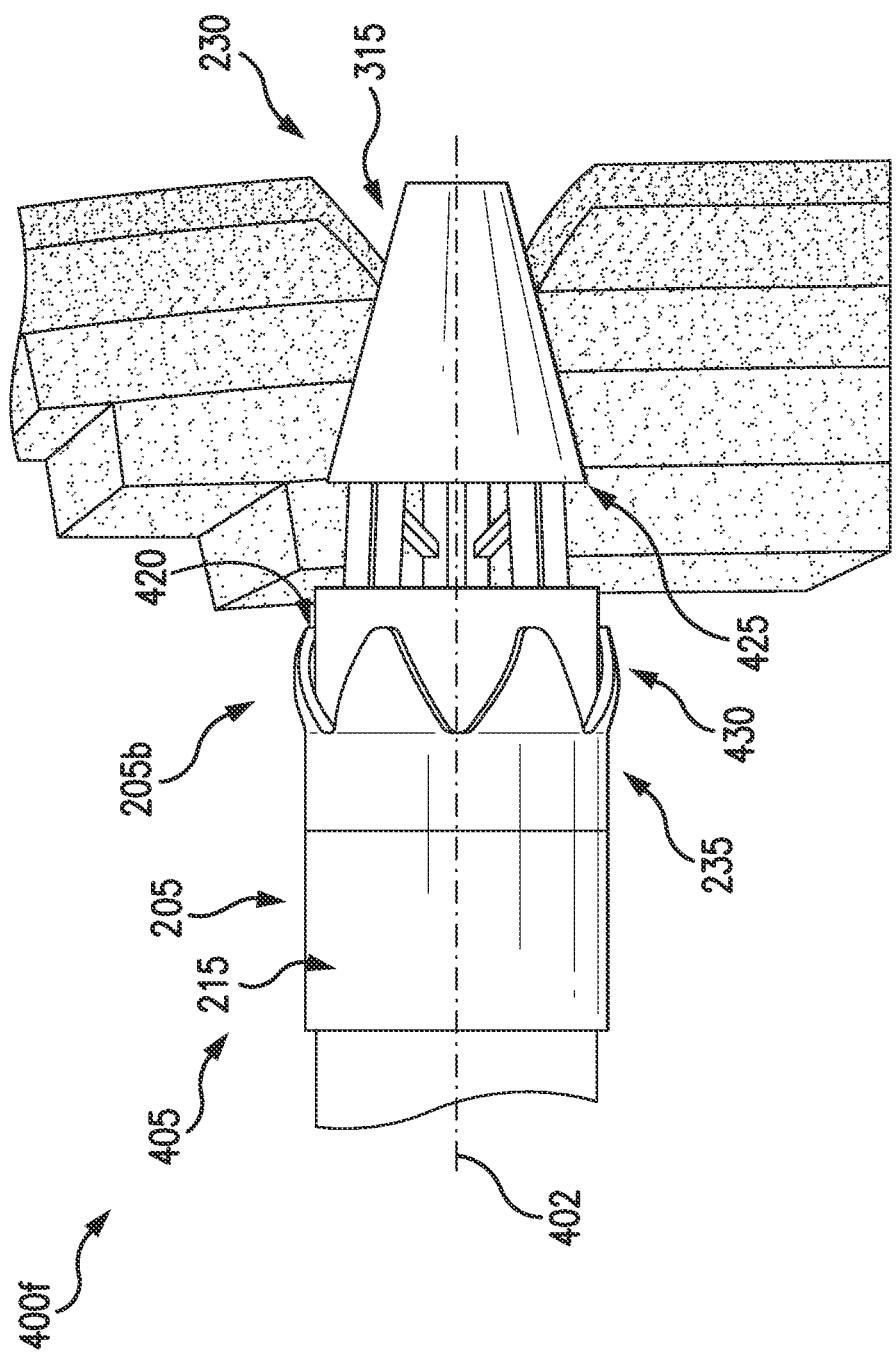

Referring now to FIG. 4F at step 400f, the tissue retractor 230 may be retracted in a proximal direction along the axis 402 into the cavity 215 of the body 205. As the arms 335, 335' and the sheath 245 are retracted into the cavity 215, the selected tissue for resection 220 is also drawn into the cavity 215. In some embodiments, the lumen 225 may be fully retracted, although in other embodiments the lumen 225 may remain at the location for visualization of the resection and closure procedures.

In some embodiments, cavity 215 may include an internal edge 250 for resecting the selected tissue 220 (see FIGS. 2A-2B). For example, the distal cap 315 may clamp the selected tissue 220 for removal against the device, and the internal edge may be advanced in a distal direction to separate, or resect, the selected tissue. In some embodiments, an edge 420 of the cavity 215 may be a shear edge (see FIG. 4F), so that as the tissue 220 is drawn into the cavity 215, the edge 420 resects, or separates, the selected tissue. In other embodiments, an edge 425 of the distal cap 315, e.g., at the proximal end 315 a, may be a shear edge, so that as the tissue 220 is drawn into the cavity, the edge 425 of the distal cap 315 resects, or separates, the selected tissue. When the tissue retractor 230 is retracted in proximal direction toward the body 205, at least a portion of the expansion mechanism may be received within the cavity, e.g., so that the proximal edge 425 of the distal cap 315 is adjacent the distal edge 420 of the cavity 215. Edges 250, 420, and/or 425 may be alternatives to each other and/or may be used in any combination for tissue resection. In embodiments where the tissue resecting device is one or more Edges 250, 420, and/or 425, tissue resection may occur when a sufficient amount of force is applied to the tissue retractor 230 to cleanly resect the tissue. In embodiments where the tissue resecting device is a blade, the blade may be formed in any shape, including but not limited to a straight blade edge, a tapered blade edge, crenellated, and/or saw tooth. In some embodiments, shear edges and/or blades may be configured to mate together. It is also understood that in other embodiments, a cauterizing tool or other electrical cutting device may be used to resect the selected tissue 220.

In embodiments, the selected tissue may be resected prior to deployment of a tissue closure device, e.g., tissue closure device 235. For example, the selected tissue may be resected, and the remaining tissue may be closed by a tissue closure device (e.g., clips and/or suturing) being delivered through the device 200. In some embodiments, the selected tissue may be resected concurrently with deployment of the tissue closure device. In other embodiments, the selected tissue may be resected after deployment of the tissue closure device. The tissue closure device 235 may be disposed on the outer surface 240 of the body 205, and may be deployable by advancing the closure device in a distal direction along the axis 402. When the tissue retractor 230 is retracted in a proximal direction into the cavity 215, the tissue closure device 235 may be advanced to the distal cap 315. The frustoconical shape, e.g., the tapered portion of the outer surface 320, may allow the tissue closure device 235 to slide off the distal end 205b of the body 205 to secure together edges 440 of the remaining body lumen tissue 445.

The tissue closure device 235 may be formed of a material having an elasticity, spring, and/or shape memory, and may be held on the body 205 in tension. For example, as indicated at reference numeral 430 in FIG. 4F, at least a portion of the tissue closure device is held in an open position so that the tissue closure device is in tension. Frictional forces between the tissue closure device 235 and the body 205 may also hold the tissue closure device 235 stationary on the body 205 until the medical professional desires to deploy the tissue closure device 235. When the tissue closure device 235 is advanced distally to engage the tissue closure device 235 around the remaining body lumen tissue, at least a portion of the tissue closure device 235 may adjust to a relaxed state as shown at reference numeral 435 in FIG. 4G. The tissue closure device 235 may be closed around the edges 440 of the remaining body lumen tissue 445. For example, at least a portion of the tissue closure device 235 may spring radially inward to secure the edges 440 of the remaining body lumen tissue 445. The spring force of the tissue closure device 235 may be sufficient to prevent slippage on the remaining body lumen tissue 445. In embodiments, the tissue closure device 235 may be configured to minimize and/or prevent tissue damage, e.g., tearing.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the subject matter of the claims.

What is claimed is:

1. A device for tissue resection from within a body lumen, comprising:
    an elongate body having a cavity at a distal end;
    a tissue retractor extendable distally from the distal end of the elongate body and including an expansion mechanism, the expansion mechanism including a plurality of arms each having a first end coupled around a distal cap and expandable radially outward from the distal cap such that an anchoring mechanism on a tip of a second end of each arm of the plurality of arms is engageable with selected tissue for resection of the body lumen;
    a tissue resecting device; and
    a tissue closure device disposed on an outer surface of the distal end of the elongate body, the tissue closure device configured to be deliverable off of the elongate body.

2. The tissue resection device according to claim 1, further comprising a sheath attached to the tissue retractor and extendable from the elongate body.

3. The tissue resection device according to claim 2, wherein the expansion mechanism further includes a plurality of connectors each having a first end coupled to the sheath and a second end coupled to a respective arm.

4. The tissue resection device according to claim 2, wherein the expansion mechanism is configured to radially expand symmetrically around the distal cap and the sheath.

5. The tissue resection device according to claim 2, wherein the expansion mechanism is configured to radially expand asymmetrically around the distal cap and the sheath.

6. The tissue resection device according to claim 1, wherein the tissue retractor is configured to extend through a wall of the body lumen, the plurality of arms positioned substantially parallel to the elongate body, and engage the selected tissue for resection when the plurality of arms is expanded radially.

7. The tissue resection device according to claim 1, wherein the tissue resecting device is an internal shear edge of the cavity, a shear proximal edge of the distal cap, or a shear edge of the distal end of the elongate body, or combinations thereof.

8. The tissue resection device according to claim 1, wherein the tissue resecting device is a mechanical cutting tool or a cauterizing tool, or combinations thereof.

9. The tissue resection device according to claim 1, wherein each arm of the plurality of arms is independently articulatable.

10. The tissue resection device according to claim 1, wherein the tissue closure device is deliverable within the body lumen.

11. A system for tissue resection from within a body lumen, comprising:
a lumen extendable into a patient, the lumen including one or more working channels for delivering accessories to selected tissue for resection of the body lumen; and
a tissue resection device deliverable over the lumen, the tissue resection device including:
an elongate body having a cavity at a distal end;
a tissue retractor extendable distally from the distal end of the elongate body and including an expansion mechanism, the expansion mechanism including a plurality of arms each having a first end coupled circumferentially around a distal cap and expandable radially outward from the distal cap such that an anchoring mechanism on a tip of a second end of each arm of the plurality of arms is engageable with the selected tissue for resection of the body lumen;
a tissue resecting device; and
a tissue closure device disposed on an outer surface of the distal end of the elongate body, the tissue closure device configured to be deliverable off of the elongate body.

12. The tissue resection system according to claim 11, wherein the tissue retractor is configured to extend through the selected tissue for resection to an outer surface of the body lumen, the plurality of arms positioned substantially parallel to the elongate body, and engaged with the outer surface when the plurality of arms is expanded radially.

13. The tissue resection system according to claim 12, wherein the tissue retractor is configured to retract the arms substantially parallel to the elongate body while the anchoring mechanisms are engaged with the outer surface of the selected tissue for resection.

14. The tissue resection system according to claim 11, wherein the tissue retractor is configured to retract proximally towards the elongate body such that the arms are receivable in the cavity.

15. The tissue resection system according to claim 11, further comprising a sheath attached to the tissue retractor and extendable from the elongate body.

16. The tissue resection system according to claim 15, wherein the sheath and the lumen are coaxial such that the sheath is extendable and retractable with respect to the elongate body along the lumen.

17. A method for resection of selected tissue in a body lumen of a patient, comprising:
positioning a distal end of a lumen in the body lumen of the patient to the selected tissue for resection;
extending a tissue resection device to the selected tissue for resection, the tissue resection device including an elongate body having a cavity at a distal end and a tissue retractor extendable distally from the distal end of the elongate body;
advancing the tissue retractor from an inner surface of the selected tissue to an outer surface of the selected tissue;
radially expanding a plurality of arms on an expansion mechanism of the tissue retractor;
engaging an anchoring mechanism on a tip of an end of each arm to the tissue selected for resection;
retracting the plurality of arms radially inward while the anchoring mechanisms are engaged to the selected tissue for resection, to capture the selected tissue;
retracting the tissue retractor in proximally toward the elongate body such that the captured tissue is received within the cavity of the elongate body;
resecting the selected tissue from the body lumen; and
delivering a tissue closure device off of an outer surface of the distal end of the elongate body.

18. The method according to claim 17, wherein the expansion mechanism further includes a plurality of connectors each having a first end coupled to a sheath distally extendable from the elongate body, and a second end coupled to a respective arm such that the plurality of arms is radially expandable by articulation of the connectors.

19. The method according to claim 17, further comprising closing remaining tissue of the body lumen with the tissue closure device.

* * * * *